United States Patent
Matsuura et al.

(10) Patent No.: US 12,428,365 B2
(45) Date of Patent: Sep. 30, 2025

(54) PRODUCTION METHOD OF ACRYLIC ACID DERIVATIVE

(71) Applicant: DAIKIN INDUSTRIES, LTD., Osaka (JP)

(72) Inventors: Makoto Matsuura, Osaka (JP); Manaho Tomioka, Osaka (JP); Michiaki Okada, Osaka (JP); Atsushi Shirai, Osaka (JP); Sumi Ishihara, Osaka (JP); Yosuke Kishikawa, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 280 days.

(21) Appl. No.: 18/119,417

(22) Filed: Mar. 9, 2023

(65) Prior Publication Data
US 2023/0234910 A1 Jul. 27, 2023

Related U.S. Application Data

(63) Continuation of application No. PCT/JP2021/033245, filed on Sep. 10, 2021.

(30) Foreign Application Priority Data

Sep. 11, 2020 (JP) ................ 2020-153119

(51) Int. Cl.
*C07C 67/317* (2006.01)

(52) U.S. Cl.
CPC .................. *C07C 67/317* (2013.01)

(58) Field of Classification Search
CPC ........ C07C 67/30; C07C 67/317; C07C 69/53
See application file for complete search history.

(56) References Cited

U.S. PATENT DOCUMENTS

| | | | |
|---|---|---|---|
| 3,262,968 A | 7/1966 | Sedlak et al. | |
| 5,231,219 A * | 7/1993 | Grison | C07C 67/343 560/210 |
| 5,972,839 A | 10/1999 | Ziemer et al. | |
| 6,258,521 B1 | 7/2001 | Mikoshiba et al. | |
| 6,462,199 B1 | 10/2002 | Mikoshiba et al. | |
| 2020/0369593 A1* | 11/2020 | Kapitan | C07C 67/343 |

FOREIGN PATENT DOCUMENTS

| | | | |
|---|---|---|---|
| CN | 102211998 | 10/2011 | |
| CN | 104478715 * | 4/2015 | C07C 67/32 |
| CN | 102731304 B * | 5/2016 | C07C 67/33 |
| CN | 105646216 | 6/2016 | |
| EP | 0 521 752 | 1/1993 | |

(Continued)

OTHER PUBLICATIONS

CN102731304 (B), Li, Xiao-quiang, Preparation method of alpha-fluoro acrylate, English translation, 4 pages (Year: 2016).*

(Continued)

*Primary Examiner* — Yate' K Cutliff
(74) *Attorney, Agent, or Firm* — Wenderoth, Lind & Ponack, L.L.P.

(57) ABSTRACT

Disclosed is a method for producing an acrylic acid derivative represented by formula (1):

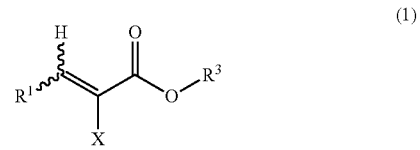

(1)

wherein
$R^1$ represents hydrogen or the like;
$R^3$ represents hydrogen or the like; and
X represents hydrogen or the like,
the method comprising step B of bringing an organic metal compound represented by formula (A3A):

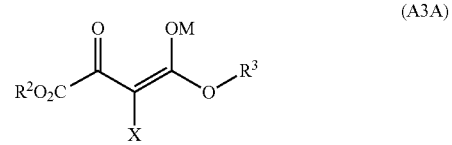

(A3A)

wherein
$R^2$, in each occurrence, is the same or different and represents hydrogen or like;
$R^3$ represents hydrogen or the like;
X represents hydrogen or the like; and
M represents hydrogen or the like, or
an organic metal compound represented by formula (A3B):

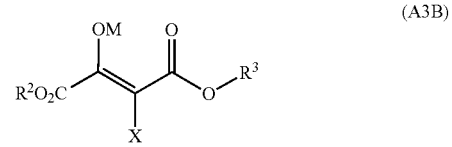

(A3B)

wherein the symbols are as defined above, or
a combination thereof, into contact with a proton donor and an aldehyde compound to obtain a compound represented by formula (1).

12 Claims, No Drawings

(56) References Cited

FOREIGN PATENT DOCUMENTS

JP          2001-506643      5/2001
WO            98/33760       8/1998

OTHER PUBLICATIONS

Organic Chemistry, Textbook for MSU, pp. 1348-1354, with English-language translation.
International Preliminary Report on Patentability issued Mar. 7, 2023, in International (PCT) Application No. PCT/JP2021/033245.
Extended European Search Report issued Oct. 1, 2024 in corresponding European Application No. 21866851.5.

* cited by examiner

PRODUCTION METHOD OF ACRYLIC ACID DERIVATIVE

TECHNICAL FIELD

The present disclosure relates to a method for producing an acrylic acid derivative and the like.

BACKGROUND ART

Acrylic acid derivatives are widely used for materials of water-absorbing polymers; materials of acrylic resins as a substitute for inorganic glass for use in window materials for buildings and vehicles, coverings for lighting equipment, lantern signs, road signs, daily necessities, office supplies, crafts, windscreens of watches, and the like; and acrylic resin coating materials. Further, fluorine-containing acrylic derivatives are useful as synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

As a method for producing an α-fluoroacrylic acid ester, Patent Literature 1 discloses a method for producing an α-fluoroacrylic acid ester by reacting equimolar amounts of $CH_2FCOOR$, wherein R is a lower alkyl group, and an aldehyde in the presence of a strong base typified by sodium methoxide.

CITATION LIST

Patent Literature

PTL 1: U.S. Pat. No. 3,262,968

SUMMARY

The present disclosure includes the following embodiments.

A method for producing an acrylic acid derivative represented by formula (1):

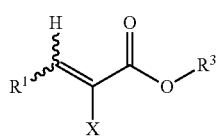

(1)

wherein $R^1$ represents a hydrogen atom, an alkyl group, a fluoroalkyl group, an aryl group optionally having one or more substituents, or a halogen atom;

$R^3$ represents a hydrogen atom, an alkyl group, a fluoroalkyl group, or an aryl group optionally having one or more substituents; and X represents a hydrogen atom, a fluoroalkyl group, an alkyl group, or a halogen atom, the method comprising step B of bringing a compound represented by formula (A3A):

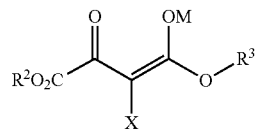

(A3A)

wherein $R^2$ represents a hydrogen atom, an alkyl group, or an aryl group;

$R^3$ is as defined above;

X is as defined above; and

M represents a hydrogen atom or a metal, or a compound represented by formula (A3B):

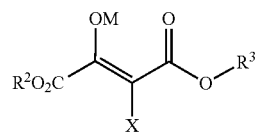

(A3B)

wherein the symbols are as defined above, or a combination thereof, into contact with a proton donor and an aldehyde compound to obtain a compound represented by formula (1).

According to the production method of the present disclosure, an acrylic acid derivative can be produced at a high conversion rate and/or a high yield.

DESCRIPTION OF EMBODIMENTS

Terms

The symbols and abbreviations in the present specification will be understood in the meaning usually used in the technical field of the present disclosure in the context of the present description, unless otherwise specified.

The term "comprising" in the present specification is used with the intention of including the meaning of the phrases "consisting essentially of" and "consisting of."

In the present specification, the term "reaction product" may be a reaction product compound or a reaction product composition.

The "reaction product composition" may contain, for example, one or more unreacted reactants etc. in addition to one or more reaction product compounds.

The steps, treatments, or operations described in the present specification can be performed at room temperature, unless otherwise specified.

The room temperature referred to in the present specification can mean a temperature in the range of 10 to 40° C.

The notation "$C_{n-m}$" (wherein n and m are each a number) written with a substituent or the like means that the number of carbon atoms in the substituent or the like is n or more and m or less, as is usually understood by persons skilled in the art.

In the present specification, "alkyl" (the term "alkyl" encompasses the "alkyl" moiety in "fluoroalkyl" or the like) may be cyclic, linear, or branched. That is, in the present specification, the term "alkyl" is intended to include, in the broad sense, cycloalkyl groups in addition to (acyclic) alkyl groups.

In the present specification, "alkyl" may be, for example, $C_{1-20}$, $C_{1-12}$, $C_{1-6}$, $C_{1-4}$, or $C_{1-3}$ alkyl.

In the present specification, specific examples of "alkyl" include methyl, ethyl, propyl, isopropyl, butyl, isobutyl, sec-butyl, tert-butyl, pentyl, neopentyl, hexyl, and like linear or branched alkyl groups.

In the present specification, specific examples of "alkyl" also include cyclopropyl, cyclobutyl, cyclopentyl, cyclohexyl, and like $C_{3-6}$ cyclic alkyl (cycloalkyl) groups.

In the present specification, "fluoroalkyl" refers to an alkyl group in which at least one hydrogen is replaced by fluorine.

In the present specification, the number of fluorine atoms in the "fluoroalkyl" may be one or more (e.g., 1 to 3, 1 to 6, 1 to 12, or 1 to the maximum replaceable number).

"Fluoroalkyl" includes perfluoroalkyl. "Perfluoroalkyl" is an alkyl group in which all hydrogen atoms are replaced by fluorine atoms.

In the present specification, "fluoroalkyl" may be, for example, $C_{1-20}$, $C_{1-12}$, $C_{1-6}$, $C_{1-4}$, or $C_{1-3}$ fluoroalkyl.

In the present specification, "fluoroalkyl" may be linear or branched.

In the present specification, specific examples of "fluoroalkyl" include fluoromethyl, difluoromethyl, trifluoromethyl, 2,2,2-trifluoroethyl, pentafluoroethyl, tetrafluoropropyl (e.g., $HCF_2CF_2CH_2$—), hexafluoropropyl (e.g., $(CF_3)_2CH$—), nonafluorobutyl, octafluoropentyl (e.g., $HCF_2CF_2CF_2CF_2CH_2$—), tridecafluorohexyl, and the like.

In the present specification, examples of "aryl" include phenyl, naphthyl, and the like.

In the present specification, examples of "halogen" include fluorine, chlorine, bromine, iodine, and the like.

Production Method

The production method of the present disclosure is a method for producing an acrylic acid derivative represented by formula (1) (which may be referred to as "acrylic acid derivative (1)" in the present specification):

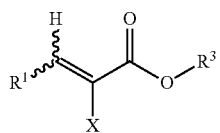

(1)

wherein
$R^1$ represents a hydrogen atom, an alkyl group, a fluoroalkyl group, an aryl group optionally having one or more substituents, or a halogen atom;
$R^3$ represents a hydrogen atom, an alkyl group, a fluoroalkyl group, or an aryl group optionally having one or more substituents; and
X represents a fluoroalkyl group, an alkyl group, a halogen atom, or a hydrogen atom,
the method comprising step B of bringing a compound represented by formula (A3A) (which may be referred to as "compound (A3A)" in the present specification):

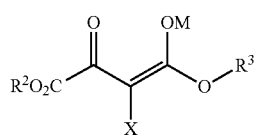

(A3A)

wherein
$R^2$ represents a hydrogen atom, an alkyl group, or an aryl group;
$R^3$ is as defined above;
X is as defined above; and
M represents a hydrogen atom or a metal, or
an organic metal compound represented by formula (A3B) (which may be referred to as "compound (A3B)" in the present specification):

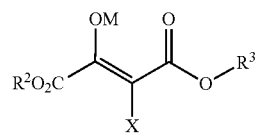

(A3B)

wherein the symbols are as defined above, or a combination thereof (in the present specification, the compounds and the combination thereof may be collectively referred to as "substance A"), into contact with a proton donor and an aldehyde compound to obtain the compound represented by formula (1).

As is usually understood by persons skilled in the art, formula (1) includes

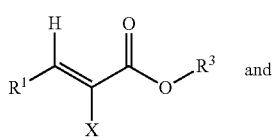

(1-a)

and

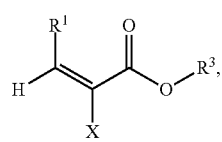

(1-b)

and a combination (or a mixture) thereof.

$R^1$ is preferably a hydrogen atom, a linear or branched $C_{1-6}$ alkyl group, or an aryl group, and more preferably a hydrogen atom or a linear or branched $C_{1-6}$ alkyl group.

$R^1$ is preferably a hydrogen atom.

$R^3$ is preferably a $C_{1-6}$ alkyl group or a $C_{1-6}$ fluoroalkyl group.

$R^3$ is preferably a $C_{1-4}$ alkyl group or a $C_{1-4}$ fluoroalkyl group. $R^3$ is preferably methyl.

X is preferably a halogen atom or a fluoroalkyl group.

X is preferably a halogen atom.

X is preferably fluorine.

M is preferably an alkali metal (e.g., Li, Na, K) or an alkaline earth metal (e.g., Ca, Sr, Ba).

Substance A can be obtained, for example, by a method comprising step A of reacting a compound represented by formula (A1): $X-CH_2-CO-O-R^3$, wherein the symbols are as defined above (which may be referred to as "compound (A1)" in the present specification) with an oxalic acid compound represented by formula (A2): $(CO_2R^2)_2$, wherein $R^2$, in each occurrence, is the same or different and represents a hydrogen atom, an alkyl group, or an aryl group (which may be referred to as "compound (A2)" in the present specification) in the presence of a base.

The base is preferably selected from the group consisting of
(1) a hydroxide of an alkali metal, an alkaline earth metal, or a transition metal;
(2) a (mono- or di-) hydrocarboxide (e.g., an alkoxide, an aryloxide) of an alkali metal, an alkaline earth metal, or a transition metal;
(3) a hydrocarbyl (e.g., aryl, alkyl) lithium;
(4) a hydrocarbyl (e.g., aryl, alkyl) sodium; and
(5) a hydrocarbyl (e.g., aryl, alkyl) metal halide.

Examples of the alkali metal, alkaline earth metal, or transition metal include zinc, iron, aluminum, titanium, zirconium, magnesium, tin, silane, and vanadium.

Specific examples of the alkoxide include $Al(O\text{-}i\text{-}C_3H_7)_3$, $Ba(OC_2H_5)_2$, $Bi(O\text{-}t\text{-}C_5H_{11})_3$, $Ca(OC_2H_5)_2$, $Fe(O\text{-}i\text{-}C_3H_7)_3$, $Ga(O\text{-}i\text{-}C_3H_7)_3$, $Ge(OC_2H_5)_4$, $Hf(O\text{-}i\text{-}C_3H_7)_4$, $In(O\text{-}i\text{-}C_3H_7)_3$, $KOC_2H_5$, $La(O\text{-}i\text{-}C_3H_7)_3$, $LiOCH_3$, $Mg(OC_2H_5)_2$, $Mo(OC_2H_5)_5$, $NaOC_2H_5$, $Nb(OC_2H_5)_5$, $Pb(O\text{-}i\text{-}C_3H_7)_2$, $Sb(OC_2H_5)_3$, $Sn(O\text{-}i\text{-}C_3H_7)_4$, $Sr(O\text{-}i\text{-}C_3H_7)_2$, $Ta(OC_2H_5)_5$, $Ti(O\text{-}i\text{-}C_3H_7)_4$, $VO(C_2H_5)_3$, $W(OC_2H_5)_5$, $Y(O\text{-}i\text{-}C_3H_7)_3$, $Zn(OC_2H_5)_2$, $Zr(O\text{-}i\text{-}C_3H_7)_4$, $Zr(O\text{-}t\text{-}C_4H_9)_4$, and $Zr(O\text{-}n\text{-}C_4H_9)_4$.

The base is preferably a strong base.

Examples of the base include
(1) a hydroxide of an alkali metal or alkaline earth metal (e.g., lithium hydroxide, sodium hydroxide, potassium hydroxide, rubidium hydroxide, cesium hydroxide, magnesium hydroxide, calcium hydroxide, strontium hydroxide);
(2) an alkoxide of an alkali metal or alkaline earth metal (e.g., an alkoxide represented by formula: ROM, wherein R is methyl, ethyl, propyl, isopropyl, n-butyl, isobutyl, sec-butyl, tert-butyl, n-pentyl, tert-pentyl, neopentyl, isopentyl, sec-pentyl, 3-pentyl, n-hexyl, tertiary carbon-containing hexyl, quaternary carbon-containing hexyl, n-heptyl, or isoheptyl; and M is sodium, potassium, or lithium);
(3) an alkyllithium (e.g., n-butyllithium, sec-butyllithium, tert-butyllithium);
(4) an alkylsodium (e.g., n-butylsodium, sec-butylsodium, tert-butylsodium); and
(5) an alkyl magnesium halide (e.g., a Grignard reagent).

The base is preferably an alkoxide represented by formula: ROM, wherein R is methyl, ethyl, propyl, isopropyl, butyl, isobutyl, pentyl, isoamyl, hexyl, or isoheptyl; and M is sodium, potassium, or lithium.

The bases may be used singly or in a combination of two or more.

The base may be generally used in an amount of 0.9 to 1.7 moles, preferably 1.0 to 1.5 moles, and more preferably 1.1 to 1.3 moles, per mole of compound (A1).

In the oxalic acid compound, it is preferred that $R^2$ is independently, in each occurrence, an alkyl group. Examples of the oxalic acid compound include dimethyl oxalate, methyl ethyl oxalate, diethyl oxalate, dipropyl oxalate, and dibutyl oxalate.

The oxalic acid compounds may be used singly or in a combination of two or more.

The oxalic acid compound may be used in an equal amount or more (preferably an excess amount) per mole of compound (A1). For example, the oxalic acid compound may be used in an amount of 0.9 to 1.7 moles, preferably 1.0 to 1.5 moles, and more preferably 1.1 to 1.2 moles, per mole of compound (A1).

The molar ratio of dimethyl oxalate and the base (preferred example: sodium methoxide) may be generally within the range of 1:10 to 10:1, preferably 1:5 to 5:1, and more preferably 1:3 to 3:1.

In an embodiment of the present disclosure, the ratio is preferably within the range of 1:3 to 1:1, 1:2.5 to 1:1, 1:2 to 1:1.01, 1:1.5 to 1:1.05, 1:1.3 to 1:1.07, or 1:1.2 to 1:1.1.

In another embodiment of the present disclosure, the ratio is preferably within the range of 3:1 to 1:1, 2.5:1 to 1:1, 2:1 to 1:1, 1.5:1 to 1.01:1, 1.3:1 to 1.05:1, or 1.2:1 to 1.07:1.

It is preferable to bring the oxalic acid compound into contact with compound (A1) wherein $R^2$ and $R^3$ are the same. In terms of versatility, diphenyl oxalate, dipropyl oxalate, dimethyl oxalate, and diethyl oxalate are preferable, and dimethyl oxalate and diethyl oxalate are more preferable.

Examples of the proton donor include water and/or an organic acid, an inorganic acid, or a solid acid.

The organic acid, the inorganic acid, or the solid acid can be used with water, and an aqueous liquid (e.g., aqueous solution, water suspension, water immersion) thereof can be used.

The proton donor may be liquid or solid.

Examples of the organic acid include acetic acid, monomethylacetic acid, trifluoroacetic acid, methanesulfonic acid, trifluoromethanesulfonic acid, phenol, benzoic acid, citric acid, succinic acid, and oxalic acid.

Examples of the inorganic acid include sulfuric acid, hydrochloric acid, nitric acid, hydriodic acid, and hydrobromic acid.

Examples of the solid acid include silica-alumina, silica-magnesia, and ion exchange resins or ion exchange membranes each having an acid group (e.g., a sulfonic acid group, carboxylic acid group).

The proton donors may be used singly or in a combination of two or more.

For example, the proton donor may be used in the form of an aqueous solution of an acid (e.g., an organic acid, an inorganic acid).

The proton donor is preferably water and/or an organic acid, and more preferably water (e.g., ion-exchanged water, pure water) or an aqueous organic acid solution.

The organic acid may be generally used in an amount of 0.01 to 0.3 moles, and preferably 0.02 to 0.25 moles, per mole of compound (A1).

The proton donor may be suitably a Brønsted acid in relation to the base.

The proton donor may be generally used in an amount of 0.01 to 0.3 moles, and preferably 0.02 to 0.25 moles, per mole of compound (A1).

$R^1$ can be derived from an aldehyde compound.

The aldehyde compound may be
[1] gaseous formaldehyde,
[2] a high-concentration (e.g., 90 mass % or more) formaldehyde aqueous solution,
[3] at least one compound selected from the group consisting of an aliphatic aldehyde and an aromatic aldehyde optionally substituted with one or more substituents,
[4] paraformaldehyde, or a combination of two or more of these.

The "aliphatic aldehyde" may be a linear or branched aliphatic aldehyde, and may be a saturated or unsaturated aliphatic aldehyde.

The aldehyde is preferably a $C_{1-20}$ (preferably $C_{1-12}$, more preferably $C_{1-6}$, even more preferably $C_{1-4}$, still even more preferably $C_{1-3}$, and particularly preferably $C_1$ or $C_2$) linear saturated aldehyde.

In the present specification, the "aliphatic aldehyde" is, for example, a compound represented by formula: R—CHO, wherein R represents an aliphatic hydrocarbon group. The aliphatic hydrocarbon group represented by R is preferably an aliphatic hydrocarbon group.

In the present specification, the "aromatic aldehyde" is, for example, a compound represented by formula: R—CHO, wherein R is an aryl group optionally substituted with one or more substituents.

R can correspond to $R^1$.

A specific preferred example of the aldehyde compound may be one or more members selected from the group consisting of formaldehyde, acetaldehyde, n-propylaldehyde, isopropylaldehyde, n-butylaldehyde, isobutylaldehyde, pivalaldehyde, n-pentylaldehyde, n-hexylaldehyde, n-heptylaldehyde, n-octylaldehyde, nonylaldehyde, decylaldehyde, undecylaldehyde, dodecylaldehyde, tridecylaldehyde, benzaldehyde, o-anisaldehyde, m-anisaldehyde, p-anisaldehyde, o-tolualdehyde, m-tolualdehyde, and p-tolualdehyde.

The paraformaldehyde compound may be a polymer composed of two or more molecules of a formaldehyde compound (e.g., formaldehyde), and may be chain-like or cyclic. Examples thereof include polyoxymethylene and 1,3,5-trioxane.

The paraformaldehyde compound (e.g., polyoxymethylene) may preferably have a number average degree of polymerization of 2 to 100.

The formaldehyde compound may be generally used in an amount of 1.0 to 1.5 moles, and preferably 1.0 to 1.2 moles, per mole of compound (A1).

The reaction time of step A is preferably within the range of 0.1 to 72 hours, more preferably within the range of 0.1 to 48 hours, and even more preferably within the range of 0.1 to 24 hours.

The lower limit of the reaction temperature in step A may be −78° C., −50° C., −40° C., −30° C., −20° C., −10° C., or 0° C.

The upper limit of the reaction temperature in step A may be 200° C., 180° C., 150° C., 120° C., 100° C., 80° C., 60° C., 40° C., or 25° C.

In step B, the reaction product obtained in step A is brought into contact with a proton donor and an aldehyde compound to obtain the compound represented by formula (1).

The means and order of the contact are not limited.

The contact of the reaction product obtained in step A with the proton donor, and the contact of the reaction product obtained in step A with the aldehyde compound may be carried out simultaneously or sequentially and may be repeated alternately.

The reaction product may be a reaction product compound or a reaction product composition. The "reaction product composition" may contain, for example, compound (A1), the base, and oxalic acid compound (A2) in addition to one or more reaction product compounds.

In step B, the compound represented by formula (1) is produced by a reaction of the reaction product obtained in step A with the aldehyde compound.

Step B can be specifically performed, for example, by introducing the proton donor and the aldehyde compound into a reaction system comprising the reaction product obtained in step A.

Specifically, for example, step B can be performed by mixing the reaction product obtained in step A with the proton donor and the aldehyde compound.

The operations of performing step A are also described later in the present specification.

Step A and step B may proceed in parallel. In other words, step B may be started before the completion of the reaction of step A. However, in terms of a high conversion rate and/or a high yield, it is preferred that step B is started after the reaction of step A is fully or almost fully completed.

Step B may be started after a predetermined time (e.g., 1 hour or more, or two hours or more) passes from the start of the reaction of step A.

After the reaction of step A, purification or removal of some or all of unwanted substances may be performed, if necessary.

The removal may be performed by using a known method, such as distilling off, rectification, filtration, or extraction.

An appropriate temperature can be selected according to a target compound to be removed by distilling off under reduced pressure. The temperature for distilling off under reduced pressure may be 100° C. or less, and preferably 50° C. or less. The lower limit of the temperature for distilling off under reduced pressure may be, for example, 0° C.

Examples of the unwanted substances include an alcohol adduct: a product in which an alcohol is added to a double bond site of the desired product, a proton adduct: a product in which a proton donor is added to a double bond site of the desired product,
a carbonic acid diester: R'—O—CO—O—R',
a monofluoroacetic acid ester,
an oxalic acid diester, and
formic acid or a formic acid ester: H—CO—O—R'
(in these formulas, R', in each occurrence, is the same or different and represents a hydrogen atom, an alkyl group, or an aryl group).

In the removal, the content of the unwanted substances can be reduced to, for example, 10 wt % or less, 5 wt % or less, 3 wt % or less, or 1 wt % or less.

In the removal, complete removal of the unwanted substances is not necessarily required. For example, the lower limit of the content of the unwanted substances may be 1 ppm.

In a preferred embodiment of the present disclosure, it is preferred that purification (or removal of some or all of the unwanted substances) is not performed after the reaction of step A.

In a particularly preferred embodiment of the present disclosure, it is preferred that the compound represented by formula (A3A) or formula (A3B) is not separated as a solid after the reaction of step A.

The separation includes separation by filtration, drying to powder, recrystallization, etc. of the compound.

Based on common technical knowledge, an intermediate or a product is often separated from a reaction system to improve the reaction yield and selectivity.

However, in this embodiment, by not performing the separation, the decomposition of the compound represented by formula (A3A) or formula (A3B) due to drying, which occurs when the compound is taken out as a solid, can be suppressed.

In addition, this embodiment has the advantage of eliminating the limitation of a reaction solvent in step A that is required for such separation, by not performing the separation.

In this embodiment, it is not necessary to separate or dry the compound represented by formula (A3A) or formula (A3B). This can improve productivity and achieve a high yield of the desired product; thus, production costs can also be reduced.

That is, in the present disclosure, contrary to common technical knowledge, high reaction yield and high selectivity can be achieved without separating an intermediate or a product from the reaction system. Further, the present disclosure rather can improve the reaction yield and selectivity and reduce production costs by not separating an intermediate or a product from the reaction system.

The reaction time of step B (or the time during which step B is performed) is preferably within the range of 0.1 to 72 hours, more preferably within the range of 0.1 to 48 hours, and even more preferably within the range of 0.1 to 24 hours.

The lower limit of the reaction temperature (or the temperature of the reaction system) in step B may be −78° C., −50° C., −40° C., −30° C., −20° C., −10° C., or 0° C.

The upper limit of the reaction temperature in step B may be 200° C., 180° C., 150° C., 120° C., 100° C., 80° C., 60° C., 40° C., or 25° C.

The reaction temperature in step B may be the same as or different from the reaction temperature in step A. In terms of simplicity of operation, it is preferred that the reaction temperature (or the temperature of the reaction system) in step B is the same, or substantially the same, as the reaction temperature in step A.

Step A and step B may be performed continuously in flow mode, may be performed in batch mode, or may be performed in one pot.

Step A and step B may each be suitably performed in the presence of a reaction solvent.

Examples of the reaction solvent include water-soluble solvents (or hydrophilic solvents or highly polar solvents), including
  alcohols such as methanol, ethanol, n-propanol, isopropanol, n-butanol, and t-butyl alcohol;
  ketones such as acetone and methyl ethyl ketone (MEK);
  ethers such as diethylether and tetrahydrofuran (THF);
  carboxylic acids such as acetic acid and propionic acid;
  sulfoxide-based solvents such as dimethyl sulfoxide (DMSO) and sulfolane;
  amide solvents such as N,N-dimethylformamide (DMF), N,N-dimethylacetamide (DMAc), 1-methyl-2-pyrrolidone (NMP), 1,3-dimethyl-2-imidazolidinone, N,N-dimethylacrylamide, N,N-dimethylacetoacetamide, N,N-diethylformamide, and N,N-diethylacetamide; and
  water; and
  a combination of two or more of these solvents.

The solvent used in step A and the solvent used in step B may be the same or different.

When the solvent used in step A contains a proton donor, part or all of the proton donor can also serve as the proton donor used in step A described above.

Examples of the solvent include
  non-aromatic hydrocarbon solvents such as pentane, hexane, heptane, octane, cyclohexane, decahydronaphthalene, n-decane, isododecane, and tridecane;
  aromatic hydrocarbon solvents such as benzene, toluene, xylene, tetralin, veratrol, diethylbenzene, methylnaphthalene, nitrobenzene, o-nitrotoluene, mesitylene, indene, and diphenyl sulfide;
  ketones such as acetone, methyl ethyl ketone, methyl isobutyl ketone, acetophenone, propiophenone, diisobutyl ketone, and isophorone;
  halogenated hydrocarbon solvents such as dichloromethane, chloroform, and chlorobenzene;
  ether solvents such as diethyl ether, tetrahydrofuran, diisopropyl ether, methyl t-butyl ether, dioxane, dimethoxyethane, diglyme, phenetole, 1,1-dimethoxycyclohexane, diisoamyl ether, and cyclopentyl methyl ether;
  ester solvents such as ethyl acetate, isopropyl acetate, diethyl malonate, 3-methoxy-3-methylbutyl acetate, γ-butyrolactone, ethylene carbonate, propylene carbonate, dimethyl carbonate, and α-acetyl-γ-butyrolactone;
  nitrile solvents such as acetonitrile and benzonitrile;
  sulfoxide-based solvents such as dimethyl sulfoxide and sulfolane; and
  amide solvents such as N,N-dimethylformamide, N,N-dimethylacetamide, 1-methyl-2-pyrrolidone, 1,3-dimethyl-2-imidazolidinone, N,N-dimethylacrylamide, N,N-dimethylacetoacetamide, N,N-diethylformamide, and N,N-diethylacetamide.

Preferred examples of the solvent include non-aromatic hydrocarbons such as heptane, octane, and cyclohexane;
  aromatic hydrocarbon solvents such as toluene and xylene;
  ether solvents such as diethyl ether, tetrahydrofuran, diisopropyl ether, methyl t-butyl ether, dioxane, dimethoxyethane, diglyme, phenetole, 1,1-dimethoxycyclohexane, diisoamyl ether, and cyclopentyl methyl ether; and
  amide solvents such as N,N-dimethylformamide, N,N-dimethylacetamide, 1-methyl-2-pyrrolidone, 1,3-dimethyl-2-imidazolidinone, N,N-dimethylacrylamide, N,N-dimethylacetoacetamide, N,N-diethylformamide, and N,N-diethylacetamide.

The reaction solvent is preferably methanol, ethanol, N,N-dimethylformamide, N,N-dimethylacetamide, dimethyl sulfoxide, tetrahydrofuran, cyclopentyl methyl ether, methyl t-butyl ether, or 1-methyl-2-pyrrolidone.

The amount of reaction solvent is generally within the range of 1 to 10 parts by weight, preferably within the range of 2 to 8 parts by weight, and more preferably within the range of 3 to 5 parts by weight, per part by weight of compound (A1).

The solvents may be used singly or in a combination of two or more.

The reaction solvents in step A and step B may be the same or different.

In the production method of the present disclosure, a stabilizer can be suitably used.

In the present specification, the term "stabilizer" may refer to a "polymerization inhibitor," a "degradation inhibitor," or a "polymerization inhibitor and degradation inhibitor." The stabilizer may be added to the reaction system at any point in time before or during the reaction in step B. Further, the point "before the reaction in step B" may refer to any point in time before or during the reaction in step A, which is performed before step B.

By performing step B in the presence of a stabilizer, the stability of the acrylic acid derivative represented by formula (1), which is a product of step B, can be improved.

Examples of the stabilizer include $C_{1-6}$ amides (e.g., N,N-dimethylformamide (DMF), N,N-dimethylacetamide (DMAC), 1-methyl-2-pyrrolidone, 1,3-dimethyl-2-imidazolidinone, N,N-dimethylacrylamide, N,N-dimethylacetoacetamide, N,N-diethylformamide, and N,N-diethylacetamide).

Other examples of the stabilizer include $C_{1-6}$ alcohols (e.g., methanol, ethanol, n-propanol, isopropanol, n-butanol, isobutanol, tert-butanol, pentanol, and hexanol).

Other examples of the stabilizer include aldehydes.

A preferred example of aldehydes may be at least one aldehyde selected from the group consisting of an aliphatic aldehyde and an aromatic aldehyde optionally substituted with one or more substituents.

The aliphatic aldehyde may be a linear or branched aliphatic aldehyde, and may be a saturated or unsaturated aliphatic aldehyde.

The aldehyde is preferably a $C_{1-20}$ (preferably $C_{1-12}$, more preferably $C_{1-6}$, even more preferably $C_{1-4}$, still even more preferably $C_{1-3}$, and particularly preferably $C_1$ or $C_2$) linear saturated aldehyde.

The aliphatic aldehyde is, for example, a compound represented by formula: R'—CHO, wherein R' represents an aliphatic hydrocarbon group. The aliphatic hydrocarbon group represented by R' is preferably an aliphatic hydrocarbon group.

The aromatic aldehyde is, for example, a compound represented by formula: R'—CHO, wherein R' represents an aryl group optionally substituted with one or more substituents.

Specifically, the aldehyde is preferably one or more members (preferably one member) selected from the group consisting of formaldehyde, acetaldehyde, n-propylaldehyde, isopropylaldehyde, n-butylaldehyde, isobutylaldehyde, pivalaldehyde, n-pentylaldehyde, n-hexylaldehyde, n-heptylaldehyde, n-octylaldehyde, nonylaldehyde, decylaldehyde, undecylaldehyde, dodecylaldehyde, tridecylaldehyde, benzaldehyde, o-anisaldehyde, m-anisaldehyde, p-anisaldehyde, o-tolualdehyde, m-tolualdehyde, p-tolualdehyde, and the like, and more preferably n-butylaldehyde.

The amount of aldehyde is preferably 0.1 moles or less, more preferably 0.05 moles or less, and even more preferably 0.02 moles or less, per mole of acrylic acid derivative (1).

Even a very small amount of aldehyde can stabilize acrylic acid derivative (1); however, the amount of aldehyde (B) is, for example, 0.0005 moles or more per mole of acrylic acid derivative (1).

The molar ratio of the acrylic acid derivative (1) and the aldehyde is preferably 1:0.1 or less, more preferably within the range of 1:0.0005 to 1:0.05, and even more preferably within the range of 1:0.0005 to 1:0.02.

Examples of the stabilizer also preferably include amine compounds such as aliphatic primary amines, aliphatic secondary amines, aliphatic tertiary amines, alicyclic secondary amines, alicyclic tertiary amines, aromatic amines, heterocyclic amines, polymer-supported amine compounds, and the like.

Examples of aliphatic primary amines include methylamine, ethylamine, propylamine, butylamine, pentylamine, hexylamine, cyclohexylamine, and ethylenediamine.

Examples of aliphatic secondary amines include dimethylamine, diethylamine, dipropylamine, dibutylamine, dipentylamine, dihexylamine, and dicyclohexylamine.

Examples of aliphatic tertiary amines include trimethylamine, triethylamine, diisopropylethylamine, tributylamine, and N,N,N',N'-tetramethylethylenediamine.

Examples of alicyclic secondary amines include piperidine, piperazine, pyrrolidine, and morpholine.

Examples of alicyclic tertiary amines include N-methylpiperazine, N-methylpyrrolidine, 5-diazabicyclo[4.3.0]nonan-5-ene, and 1,4-diazabicyclo[2.2.2]octane.

Examples of aromatic amines include aniline, methylaniline, dimethylaniline, N,N-dimethylaniline, haloaniline, and nitroaniline.

Examples of heterocyclic amines include pyridine, melamine, pyrimidine, piperazine, quinoline, and imidazole.

Examples of polymer-supported amine compounds include polyallylamine and polyvinylpyridine.

Further, examples of stabilizers other than the above stabilizers (i.e., stabilizers other than amine compounds) include at least one compound (which may be referred to as "compound (C)" in the present specification) selected from the group (which may be referred to as "compound group (C) in the present specification) consisting of:

(1) compounds having one or more hydroxyl groups,
(2) compounds having one or more sulfide bonds,
(3) compounds having one or more thiophenolic or thiol sulfur atoms,
(4) sulfurous acid compounds, and
(5) nitrous acid compounds.

One kind of compound (C) may be used singly, or a combination of two or more kinds of compound (C) may be used.

Examples of "(1) compounds having one or more hydroxyl groups" above include alcohols represented by formula: R'—OH (wherein R' represents, for example, a $C_{1-6}$ alkyl group), such as methanol, ethanol, isopropyl alcohol, and t-butanol; and compounds having, as a partial structure, a benzene ring substituted with one or more hydroxyl groups (the hydroxyl group may be an oxo group (O=) due to tautomerism; the compounds preferably have 6 to 20 carbon atoms), such as phenol, hydroquinone, 4-methoxyphenol, 2,5-di-tert-butylhydroquinone, methylhydroquinone, tert-butylhydroquinone (TBH), p-benzoquinone, methyl-p-benzoquinone, tert-butyl-p-benzoquinone, 2,5-diphenyl-p-benzoquinone, and 2,6-di-tert-butyl-4-methylphenol (BHT) (these compounds may be referred to simply as phenol compounds).

Examples of the "(2) compounds having one or more sulfide bonds" above include dialkyl sulfides (the numbers of carbon atoms of the two "alkyls" are the same or different, and are preferably 1 to 6); and compounds having a diphenyl sulfide structure (e.g., compounds with one or more sulfide bonds having a phenyl sulfide structure and 6 to 20 carbon atoms, such as diphenyl sulfide and phenothiazine.

Examples of the "(3) compounds having one or more thiophenolic or thiol sulfur atoms" above include compounds represented by formula: R(—SH)$_n$ (wherein R represents, for example, $C_{1-6}$ alkane or $C_{6-12}$ aromatic carbocycle (e.g., benzene, diphenyl); and n represents, for example, an integer of 1 or 2), such as thiophenol, benzenedithiol, 1,2-ethanedithiol, and 1,3-propanedithiol.

Examples of the "(4) sulfurous acid compounds" above include potassium sulfite, calcium sulfite, sodium hydrogensulfite, sodium sulfite, barium sulfite, magnesium sulfite, dimethyl sulfite, diethyl sulfite, diamyl sulfite, dipropyl sulfite, and diisopropyl sulfite.

Examples of the "(5) nitrous acid compounds" above include potassium nitrite, sodium nitrite, methyl nitrite, ethyl nitrite, amyl nitrite, propyl nitrite, and isopropyl nitrite.

Compound (C) described above as a stabilizer is preferably the "(1) compound having one or more hydroxyl groups" above, and more preferably a phenol compound.

Preferred examples of the stabilizer include diisopropylethylamine, tributylamine, triethylamine, 4-methoxyphenol, 2,6-di-tert-butyl-4-methylphenol (BHT), pyridine, melamine, and phenothiazine.

The stabilizers may be used singly or in a combination of two or more.

In a preferred embodiment of the present disclosure, step B is performed in the presence of (1) one or more amine compounds and (2) one or more compounds (C), each of which can function as a stabilizer.

When a stabilizer is used in step B, the total amount thereof is preferably within the range of 100 to 50000 ppm (w/w), more preferably within the range of 100 to 10000 ppm (w/w), even more preferably within the range of 100 to 5000 ppm (w/w), still even more preferably within the range of 100 to 3000 ppm (w/w), particularly preferably within the range of 500 to 2000 ppm (w/w), and further particularly preferably within the range of 500 to 1500 ppm (w/w), relative to the acrylic acid derivative represented by formula (1).

The reactions of step A and step B may be performed, for example, in the presence of air.

The acrylic acid derivative obtained by the production method of the present disclosure may optionally be purified by a known purification method, such as solvent extraction, washing with water and dehydration, drying, filtration, distillation, concentration, and a combination thereof, depending on the use thereof.

According to the present disclosure, even when step A and step B are performed in one pot, the compound represented by formula (1) can be obtained at a high conversion rate and/or a high yield. This is related to reacting the reaction product obtained in step A with the formaldehyde compound in the presence of the proton donor in the present disclosure.

In the production method of the present disclosure, the compound represented by formula (1) can be obtained at a conversion rate preferably within the range of 80 to 98%, and more preferably within the range of 85 to 95%.

In the production method of the present disclosure, the compound represented by formula (1) can be obtained at a yield preferably within the range of 80 to 98%, and more preferably within the range of 85 to 95%.

To the reaction system of step A,
compound (A2), then the base, and then compound (A1), in this order,
compound (A2), then compound (A1), and then the base, in this order,
the base, then compound (A2), and then compound (A1), in this order,
the base, then compound (A1), and then compound (A2), in this order,
compound (A1), then the base, and then compound (A2), in this order, or
compound (A1), then compound (A2), and then the base, in this order,
may be added.

These components may be added to the reaction system of step A in any manner. For example, the components may be directly added as they are or may be dissolved or dispersed in a solvent and added;
the components may be added at one time or in multiple portions (e.g., 2 portions, 3 portions, 4 portions, 5 portions, 6 portions, 7 portions, 8 portions, 9 portions, 10 portions, 15 portions, 20 portions, 25 portions, 30 portions, 35 portions, 40 portions, 45 portions, 50 portions, 55 portions, 60 portions, 65 portions, 70 portions, 75 portions, 80 portions, 85 portions, 90 portions, 95 portions, 100 portions);
divided portions of two of these multiple kinds of materials may be added alternately;
divided portions of the same kind of material may be added repeatedly two or more times; and
any combination of these methods may be used.

To the reaction system of step B,
the proton donor, then compound (A3A) and/or (A3B), and then the formaldehyde compound, in this order,
the proton donor, then the formaldehyde compound, and then compound (A3A) and/or (A3B), in this order,
compound (A3A) and/or (A3B), then the proton donor, and then the formaldehyde compound, in this order,
the formaldehyde compound, then compound (A3A) and/or (A3B), and then the proton donor, in this order,
compound (A3A) and/or (A3B), then the formaldehyde compound, and then the proton donor, in this order, or
the formaldehyde compound, then the proton donor, and then compound (A3A) and/or (A3B), in this order,
may be added.

These components may be added to the reaction system of step B in any manner. For example, the components may be directly added as they are or may be dissolved or dispersed in a solvent and added;
the components may be added at one time or in multiple portions (e.g., 2 portions, 3 portions, 4 portions, 5 portions, 6 portions, 7 portions, 8 portions, 9 portions, 10 portions, 15 portions, 20 portions, 25 portions, 30 portions, 35 portions, 40 portions, 45 portions, 50 portions, 55 portions, 60 portions, 65 portions, 70 portions, 75 portions, 80 portions, 85 portions, 90 portions, 95 portions, 100 portions);
divided portions of two of these multiple kinds of materials may be added alternately;
divided portions of the same kind of material may be added repeatedly two or more times; and
any combination of these methods may be used.

The orders of the operations of step A or a part thereof and the operations of step B or a part thereof may be repeated any number of times and in any combination as long as the effect of the present disclosure is not significantly impaired.

The present disclosure includes the following embodiments.

Item 1.

A method for producing an acrylic acid derivative represented by formula (1):

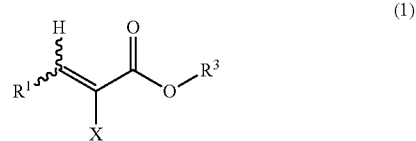

wherein
$R^1$ represents a hydrogen atom, an alkyl group, a fluoroalkyl group, an aryl group optionally having one or more substituents, or a halogen atom;
$R^3$ represents a hydrogen atom, an alkyl group, a fluoroalkyl group, or an aryl group optionally having one or more substituents; and
X represents a hydrogen atom, a fluoroalkyl group, an alkyl group, or a halogen atom,
the method comprising step B of bringing a compound represented by formula (A3A):

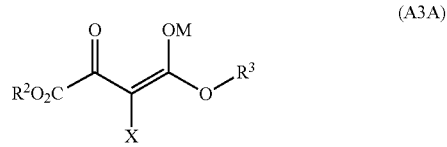

wherein
R² represents a hydrogen atom, an alkyl group, or an aryl group;
R³ is as defined above;
X is as defined above; and
M represents a hydrogen atom or a metal, or
a compound represented by formula (A3B):

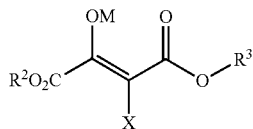

(A3B)

wherein the symbols are as defined above, or
a combination thereof, into contact with a proton donor and an aldehyde compound to obtain a compound represented by formula (1).

Item 2.

The production method according to Item 1, wherein $R^1$ is a hydrogen atom, a linear or branched $C_{1-6}$ alkyl group, or an aryl group.

Item 3.

The production method according to Item 2, wherein $R^1$ is a hydrogen atom or a linear or branched $C_{1-6}$ alkyl group.

Item 4.

The production method according to any one of Items 1 to 3, wherein $R^3$ is a $C_{1-6}$ alkyl group or a $C_{1-6}$ fluoroalkyl group.

Item 5.

The production method according to Item 4, wherein $R^3$ is a $C_{1-4}$ alkyl group or a $C_{1-4}$ fluoroalkyl group.

Item 6.

The production method according to any one of Items 1 to 5, wherein X is a halogen atom or a fluoroalkyl group.

Item 7.

The production method according to Item 6, wherein X is a halogen atom.

Item 8.

The production method according to Item 6, wherein X is a fluorine atom.

Item 9.

The production method according to any one of Items 1 to 8, further comprising step A of reacting a compound represented by formula (A1): X—CH₂—CO—O—R³, wherein the symbols are as defined above, with an oxalic acid compound represented by formula (A2): (CO₂R²)₂, wherein R², in each occurrence, is the same or different and represents a hydrogen atom, an alkyl group, or an aryl group, in the presence of a base to obtain the compound represented by formula (A3A) or the compound represented by formula (A3B), or a combination thereof.

Item 10.

The production method according to Item 9, wherein the base is at least one base selected from the group consisting of
(1) a hydroxide of an alkali metal or alkaline earth metal;
(2) an alkoxide of an alkali metal or alkaline earth metal;
(3) an alkyllithium;
(4) an alkylsodium; and
(5) an alkyl metal halide.

Item 11.

The production method according to Item 10, wherein the base is an alkoxide represented by formula: ROM, wherein R is methyl, ethyl, propyl, isopropyl, n-butyl, isobutyl, sec-butyl, tert-butyl, n-pentyl, tert-pentyl, neopentyl, isopentyl, sec-pentyl, 3-pentyl, n-hexyl, tertiary carbon-containing hexyl, quaternary carbon-containing hexyl, n-heptyl, or isoheptyl; and M is sodium, potassium, or lithium.

Item 12.

The production method according to any one of Items 9 to 11, wherein $R^2$ independently represents, in each occurrence, an alkyl group.

Item 13.

The production method according to any one of Items 1 to 12, wherein the proton donor is water and/or an organic acid, an inorganic acid, or a solid acid.

Item 14.

The production method according to Item 13, wherein the proton donor is water and/or an organic acid.

Item 15.

The production method according to any one of Items 9 to 14, wherein after the reaction of step A, the compound represented by formula (A3A) or formula (A3B) is not separated as a solid.

EXAMPLES

The present disclosure is described in more detail below with reference to Examples. However, the present disclosure is not limited to the Examples.

The meanings and structural formulas of symbols and abbreviations in the Examples are shown below.

DMF: N,N-dimethylformamide
DMSO: dimethyl sulfoxide
NMP: 1-methyl-2-pyrrolidone

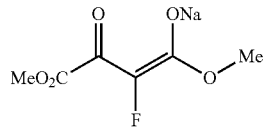

A4A structural formula

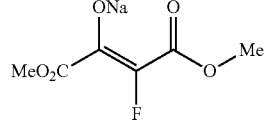

A4B structural formula

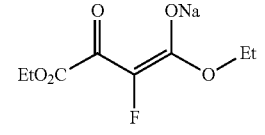

A5A structural formula

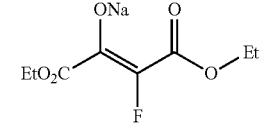

A5B structural formula

-continued

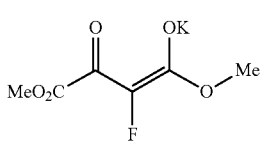

A6A structural formula

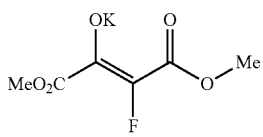

A6B structural formula

Example A-1

92 g of NMP was placed in a three-necked round-bottom flask. The flask was purged with nitrogen and placed in a water bath to set the internal temperature to 20° C. or less.

177 g of dimethyl oxalate was weighed and added to the flask. Subsequently, 70 g of sodium methoxide was weighed and added to the flask. Then, 92 g of methyl fluoroacetate was weighed and added to the flask. The mixture was stirred at room temperature for 24 hours, and the reaction was aged to quantitatively obtain a solution of substance A (A4A and A4B in this Example), which is a substance having a structure corresponding to the substrates.

Example A-2

92 g of NMP was placed in a three-necked round-bottom flask. The flask was purged with nitrogen and placed in a water bath to set the internal temperature to 20° C. or less.

119 g of dimethyl oxalate was weighed and added to the flask. Subsequently, 54 g of sodium methoxide was weighed and added to the flask. Then, 92 g of methyl fluoroacetate was weighed and added to the flask. The mixture was stirred at room temperature for 24 hours, and the reaction was aged to obtain a solution of substance A (A4A and A4B in this Example), which is a substance having a structure corresponding to the substrates, at a yield of 978. Thereafter, the pressure was reduced under conditions of 50° C. and 10 kPa. The GC area value of methanol after removal by gas chromatography was confirmed to be 30% when compared before and after the above treatment. The weight of the reaction solution after the above treatment was confirmed to be 312 g.

Example A-3

106 g of NMP was placed in a three-necked round-bottom flask. The flask was purged with nitrogen and placed in a water bath to set the internal temperature to 20° C. or less.

219 g of diethyl oxalate was weighed and added to the flask. Subsequently, 116 g of sodium ethoxide was weighed and added to the flask. Then, 106 g of ethyl fluoroacetate was weighed and added to the flask. The mixture was stirred at room temperature for 24 hours, and the reaction was aged to quantitatively obtain a solution of substance A (A5A and A5B in this Example), which is a substance having a structure corresponding to the substrates.

Example A-4

92 g of NMP was placed in a three-necked round-bottom flask. The flask was purged with nitrogen and placed in a water bath to set the internal temperature to 20° C. or less.

119 g of dimethyl oxalate was weighed and added to the flask. Subsequently, 105 g of potassium methoxide was weighed and added to the flask. Then, 92 g of methyl fluoroacetate was weighed and added to the flask. The mixture was stirred at room temperature for 24 hours, and the reaction was aged to quantitatively obtain a solution of substance A (A6A and A6B in this Example), which is a substance having a structure corresponding to the substrates.

Example A-5

92 g of DMSO was placed in a three-necked round-bottom flask. The flask was purged with nitrogen and placed in a water bath to set the internal temperature to 30° C. or less.

177 g of dimethyl oxalate was weighed and added to the flask. Subsequently, 70 g of sodium methoxide was weighed and added to the flask. Then, 92 g of methyl fluoroacetate was weighed and added to the flask. The mixture was stirred at room temperature for 24 hours, and the reaction was aged to quantitatively obtain a solution of substance A (A4A and A4B in this Example), which is a substance having a structure corresponding to the substrates.

Example A-6

92 g of DMF was placed in a three-necked round-bottom flask. The flask was purged with nitrogen and placed in a water bath to set the internal temperature to 20° C. or less.

177 g of dimethyl oxalate was weighed and added to the flask. Subsequently, 70 g of sodium methoxide was weighed and added to the flask. Then, 92 g of methyl fluoroacetate was weighed and added to the flask. The mixture was stirred at room temperature for 24 hours, and the reaction was aged to quantitatively obtain a solution of substance A (A4A and A4B in this Example), which is a substance having a structure corresponding to the substrates.

Step B

The following Examples B-1 to B-12 and Comparative Example 1 were performed using the reaction mixtures obtained in Examples A-1 to A-6.

Example B-1

431 g of NMP and 1 g of water were added to 431 g of the solution of Example A-1 in a three-necked round-bottom flask, and then, 30 g of paraformaldehyde was added in three portions. Thereafter, the reaction was aged at room temperature for 24 hours to obtain desired compound (1) (i.e., 2-fluoroacrylic acid methyl ester) having a structure corresponding to the substrates, at a yield of 89%.

The solution after the reaction obtained in the above step was subjected to gas chromatography to check by-products other than compound (1) and unreacted starting materials.

The results confirmed the following: desired compound: 89.0%; formic acid ester: 0.2% (the ester moiety was the same as the ester moiety of the desired product); carbonic acid diester: 0.5% (the ester moiety was the same as the ester moiety of the desired product); fluoroacetic acid ester: 1.0% (the ester moiety was the same as the ester moiety of the desired product); alcohol addition product of compound (1): 4.5%; and proton donor addition product of compound (1): 4.8%.

The alcohol addition product is a product in which an alcohol corresponding to the ester group is added to a double bond site of the desired product, and the proton donor addition product is a product in which a proton donor is added to a double bond site of the desired product.

Example B-2

1155 g of NMP and 1 g of water were added to 431 g of the solution of Example A-1 in a three-necked round-bottom flask, and then, 30 g of paraformaldehyde was added in 30 portions. Thereafter, the reaction was aged at room temperature for 24 hours to obtain desired compound (1) (i.e., 2-fluoroacrylic acid methyl ester) having a structure corresponding to the substrates, at a yield of 93%.

Example B-3

431 g of NMP and 4 g of water were added to 431 g of the solution of Example A-1 in a three-necked round-bottom flask, and then, 30 g of paraformaldehyde was added in three portions. Thereafter, the reaction was aged at room temperature for 24 hours to obtain desired compound (1) (i.e., 2-fluoroacrylic acid methyl ester) having a structure corresponding to the substrates, at a yield of 87%.

Example B-4

431 g of NMP was added to 431 g of the solution of Example A-1 in a three-necked round-bottom flask, and then, paraformaldehyde obtained by adding 1 g of water to 30 g of paraformaldehyde was added in three portions. The reaction was aged at room temperature for 24 hours to obtain desired compound (1) (i.e., 2-fluoroacrylic acid methyl ester) having a structure corresponding to the substrates, at a yield of 90%.

Example B-5

431 g of the solution of Example A-1 and 431 g of NMP were added to a three-necked round-bottom flask. Subsequently, 10 g of paraformaldehyde and 0.3 g of water were added simultaneously. Simultaneous addition of 10 g of paraformaldehyde and 0.3 g of water was repeated so that a total of 30 g of paraformaldehyde and a total 0.9 g of water were added. The reaction was aged at room temperature for 24 hours to obtain desired compound (1) (i.e., 2-fluoroacrylic acid methyl ester) having a structure corresponding to the substrates, at a yield of 89%.

Example B-6

431 g of NMP was added to a three-necked round-bottom flask. Subsequently, 30 g of paraformaldehyde and 1 g of water were added. 431 g of the solution of Example A-1 was added dropwise to the flask. The reaction was aged at room temperature for 24 hours to obtain desired compound (1) (i.e., 2-fluoroacrylic acid methyl ester) having a structure corresponding to the substrates, at a yield of 90%.

Example B-7

312 g of NMP and 1 g of water were added to 312 g of the solution of Example A-2 in a three-necked round-bottom flask, and then, 30 g of paraformaldehyde was added in three portions. The reaction was aged at room temperature for 24 hours to obtain desired compound (1) (i.e., 2-fluoroacrylic acid methyl ester) having a structure corresponding to the substrates, at a yield of 88%.

Example B-8

547 g of NMP and 1 g of water were added to 547 g of the solution of Example A-3 in a three-necked round-bottom flask, and then, 30 g of paraformaldehyde was added in three portions. The reaction was aged at room temperature for 24 hours to obtain desired compound (1) (i.e., 2-fluoroacrylic acid ethyl ester) having a structure corresponding to the substrates, at a yield of 89%.

Example B-9

408 g of NMP and 1 g of water were added to 408 g of the solution of Example A-4 in a three-necked round-bottom flask, and 30 g of paraformaldehyde was added in three portions. The reaction was aged at room temperature for 24 hours to obtain desired compound (1) (i.e., 2-fluoroacrylic acid methyl ester) having a structure corresponding to the substrates, at a yield of 88%.

Example B-10

385 g of DMSO and 1 g of water were added to 385 g of the solution of Example A-5 in a three-necked round-bottom flask, and then, 30 g of paraformaldehyde was added in three portions. The reaction was aged at room temperature for 24 hours to obtain desired compound (1) (i.e., 2-fluoroacrylic acid methyl ester) having a structure corresponding to the substrates, at a yield of 90%.

Example B-11

431 g of DMF and 1 g of water were added to 431 g of the solution of Example A-6 in a three-necked round-bottom flask, and then, 30 g of paraformaldehyde was added in three portions. The reaction was aged at room temperature for 24 hours to obtain desired compound (1) (i.e., 2-fluoroacrylic acid methyl ester) having a structure corresponding to the substrates, at a yield of 91%.

Comparative Example 1

431 g of NMP was added to 431 g of the solution of Example A-1 in a three-necked round-bottom flask, and then, 30 g of paraformaldehyde was added in three portions. Thereafter, the reaction was aged at room temperature for 24 hours to obtain desired compound (1) (i.e., 2-fluoroacrylic acid methyl ester) having a structure corresponding to the substrates, at a yield of 30%.

The invention claimed is:
1. A method for producing an acrylic acid derivative represented by formula (1):

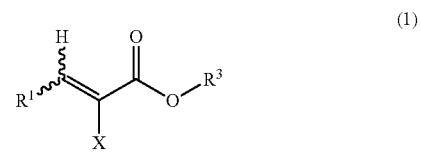

wherein

R¹ represents a hydrogen atom, an alkyl group, a fluoroalkyl group, an aryl group optionally having one or more substituents, or a halogen atom;

R³ represents a hydrogen atom, an alkyl group, a fluoroalkyl group, or an aryl group optionally having one or more substituents; and X represents a hydrogen atom, a fluoroalkyl group, an alkyl group, or a halogen atom, the method comprising step A of reacting a compound represented by formula (A1): X—CH₂—CO—O—R³, wherein the symbols are as defined above, with an oxalic acid compound represented by formula (A2): $(CO_2R^2)_2$, wherein $R^2$, in each occurrence, is the same or different and represents a hydrogen atom, an alkyl group, or an aryl group, in the presence of a base to obtain a compound represented by formula (A3A):

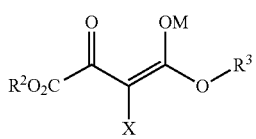

(A3A)

wherein $R^2$ is as defined above;
$R^3$ is as defined above;
X is as defined above; and
M represents a hydrogen atom or a metal, or
a compound represented by formula (A3B):

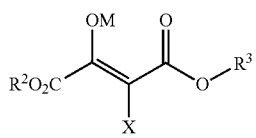

(A3B)

wherein the symbols are as defined above, or
a combination thereof, and step B of bringing the compound represented by formula (A3A), or the compound represented by formula (A3B), or a combination thereof into contact with a proton donor and an aldehyde compound to obtain a compound represented by formula (1), wherein the proton donor is water and the proton donor is used in an amount of 0.01 to 0.3 moles per mole of compound (A1).

2. The production method according to claim 1, wherein $R^1$ is a hydrogen atom, a linear or branched $C_{1-6}$ alkyl group, or an aryl group.

3. The production method according to claim 2, wherein $R^1$ is a hydrogen atom or a linear or branched $C_{1-6}$ alkyl group.

4. The production method according to claim 1, wherein $R^3$ is a $C_{1-6}$ alkyl group or a $C_{1-6}$ fluoroalkyl group.

5. The production method according to claim 4, wherein $R^3$ is a $C_{1-4}$ alkyl group or a $C_{1-4}$ fluoroalkyl group.

6. The production method according to claim 1, wherein X is a halogen atom or a fluoroalkyl group.

7. The production method according to claim 6, wherein X is a halogen atom.

8. The production method according to claim 6, wherein X is a fluorine atom.

9. The production method according to claim 1, wherein the base is at least one base selected from the group consisting of (1) a hydroxide of an alkali metal or alkaline earth metal;
(2) an alkoxide of an alkali metal or alkaline earth metal;
(3) an alkyllithium;
(4) an alkylsodium; and
(5) an alkyl metal halide.

10. The production method according to claim 9, wherein the base is an alkoxide represented by formula: ROM, wherein R is methyl, ethyl, propyl, isopropyl, n-butyl, isobutyl, sec-butyl, tert-butyl, n-pentyl, tert-pentyl, neopentyl, isopentyl, sec-pentyl, 3-pentyl, n-hexyl, tertiary carbon-containing hexyl, quaternary carbon-containing hexyl, n-heptyl, or isoheptyl; and M is sodium, potassium, or lithium.

11. The production method according to claim 1, wherein $R^2$ independently represents, in each occurrence, an alkyl group.

12. The production method according to claim 1, wherein after the reaction of step A, the compound represented by formula (A3A) or formula (A3B) is not separated as a solid.

* * * * *